US005773659A

United States Patent [19]
Fukatsu et al.

[11] Patent Number: 5,773,659
[45] Date of Patent: Jun. 30, 1998

[54] PROCESS FOR PRODUCING DIMETHYLAMINE

[75] Inventors: Michio Fukatsu, Tokyo-to; Katsumasa Nishijima, Kanagawa-ken; Takeshi Narita, Kanagawa-ken; Toshio Nakamura, Kanagawa-ken; Kiyonobu Niwa, Tokyo-to, all of Japan

[73] Assignee: Nitto Kagaku Kogyo Kabushiki Kaisha, Tokyo-to, Japan

[21] Appl. No.: 682,588

[22] PCT Filed: Dec. 5, 1995

[86] PCT No.: PCT/JP95/02480

§ 371 Date: Jul. 24, 1996

§ 102(e) Date: Jul. 24, 1996

[87] PCT Pub. No.: WO96/17820

PCT Pub. Date: Jun. 13, 1996

[30] Foreign Application Priority Data

Dec. 7, 1994 [JP] Japan ................................ 6-330360
Nov. 21, 1995 [JP] Japan ................................ 7-325284

[51] Int. Cl.⁶ .................................................. C07C 209/16
[52] U.S. Cl. ................................................ 564/479; 564/470
[58] Field of Search ................................... 564/479, 470

[56] References Cited

U.S. PATENT DOCUMENTS 4,918,233  4/1990  Deeba et al. ........................ 564/479

FOREIGN PATENT DOCUMENTS 57-169444  10/1982  Japan.
57-171436  10/1982  Japan.

*Primary Examiner*—Brian M. Burn
*Attorney, Agent, or Firm*—Wenderoth, Lind & Ponack

[57] ABSTRACT

To develop a zeolite catalyst which can prevent the drastic lowering of dimethylamine selectivity to be caused in the production of dimethylamine using a zeolite catalyst when the conversion of methanol is high, and which can give higher dimethylamine selectivity and lower trimethylamine selectivity as well as higher methanol-consuming reaction activity; and to provide a process for producing dimethylamine with high selectivity, using the catalyst.

A process for producing dimethylamine by allowing methanol, or methanol and a methylamine mixture, or a methylamine mixture to react with ammonia in the gaseous phase in the presence of a catalyst, characterized in that a modified zeolite prepared by treating a zeolite with a solution containing a chelating agent is used as the catalyst.

9 Claims, No Drawings

PROCESS FOR PRODUCING DIMETHYLAMINE

FIELD OF THE ART

The present invention relates to a process for producing dimethylamine, utilizing the gas phase catalytic reaction between methanol and ammonia. More particularly, the present invention relates to a process for producing dimethylamine, characterized by using a specific catalyst.

Dimethylamine is an important chemical intermediate useful in the production of a variety of solvents, pharmaceuticals, rubber chemicals and surface active agents.

BACKGROUND ART

Typically, dimethylamine is produced by carrying out the reaction between methanol and ammonia in the gaseous phase at a high temperature (approximately 400° C.) in the presence of a solid acid catalyst, such as alumina or silica alumina, capable of causing dehydration and amination. In addition to dimethylamine (hereinafter referred to as DMA), monomethylamine (hereinafter referred to as MMA) and trimethylamine (hereinafter referred to as TMA) are produced as by-products by this reaction. The demand for these by-product methylamines is considerably smaller than that for DMA. For this reason, after being separated from the reaction product, these by-products are transferred to the reaction system and reused.

Distillation is conducted in order to isolate dimethylamine from the methylamine reaction product. However, TMA forms complicated azeotropic mixtures with ammonia, MMA and DMA, so that a very intricate, large-scale distillation operation is needed. As a result, the cost for energy to be consumed by the process of recovering DMA amounts extremely high. The recovery process is shown in detail, for instance, in "Manufacturing Process Charts, Revised Edition" (in Japanese) (published by Kabushiki Kaisha Kagaku Kogyo-Sha on Apr. 25, 1978).

In order to reduce the production cost of DMA and to make the size of the equipment smaller, it is essential to suppress, as much as possible, the formation of the by-product methylamines, especially the formation of TMA, and to promote the formation of DMA. However, the selectivities of the three methylamines are thermodynamically determined on the above-described conventional amorphous solid acid catalyst such as alumina or silica alumina. Under the typical reaction conditions, the rate of TMA formation is considerably higher than that of DMA formation.

For instance, in the case where the reaction temperature is 400° C. and the ratio of ammonia to methanol at the inlet of a reactor is 1:1 (weight ratio), the weight ratio of the amines formed at equilibrium, calculated thermodynamically is MMA:DMA:TMA=0.284:0.280:0.436. It is therefore necessary to continually separate a large amount of MMA and TMA, and to recirculate, in the reaction system, these two methylamines along with a large amount of excess ammonia which is to exist so that the reaction can proceed favorably to DMA from the viewpoint of equilibrium.

In recent years, various zeolite catalysts have been proposed in order to solve the above problem. For example, there can be mentioned Japanese Laid-Open Patent Publication No. 69846/1981 which relates to zeolite A; Japanese Laid-Open Patent Publications Nos. 148708/1979 and 69846/1983 which relate to FU-1; U.S. Pat. No. 4,082,805 which relates to ZSM-5; Japanese Laid-Open Patent Publication No. 113747/1981 which relates to ferrierite and erionite; Japanese Laid-Open Patent Publications Nos. 178951/1986 and 8358/1988 which relate to rho, ZK-5 and chabazite; and Japanese Laid-Open Patent Publications Nos. 46846/1981, 210050/1984 and 049340/1983 which relate to mordenite.

Although all of the processes using the above zeolite catalysts may give DMA selectivities higher than the thermodynamical equilibrium values, the DMA selectivities and the suppression of TMA formation are not always sufficient. In addition, there is still remaining such a problem that the DMA selectivity is, in general, drastically lowered when the conversion of methanol exceeds 95–96%, so that it is required to continually keep a considerable amount of unreacted methanol so as to maintain the DMA selectivity high. For example, Japanese Laid-Open Patent Publication No. 210050/1984 discloses a process for selectively produce DMA in which the reaction is carried out by using Na-mordenite at a conversion of methanol of 80 to 96%. This process can give excellent DMA selectivity and methanol-consuming reaction activity as compared with the processes using the zeolite catalysts proposed in the past. According to this process, when the N/C ratio is in the preferred range of 1 to 2.5 and the conversion of methanol is 80% or higher, good results can be obtained, for instance, DMA is 53.0% by weight while TMA is 7.7% by weight (conversion of methanol: 86.1%, SV: 2010); and DMA is 53.9% by weight while TMA is 12.9% by weight (conversion of methanol: 94.1%, SV: 2020).

Further, in many cases, the activity (methanol-consuming reaction rate) and the selectivity may not be consistent with each other; in order to keep the selectivity high, it may be necessary to sacrifice the activity to a certain extent, and, on the contrary, in order to keep the activity high, it is needed to sacrifice the selectivity to a certain degree. For example, in Example 1 of the above-described Japanese Laid-Open Patent Publication No. 210050/1984, when the DMA selectivity is increased from 39.5% by weight to 49.3% by weight by controlling the alkaline cations of the zeolite catalyst, the reaction activity at the conversion of methanol of approximately 90% is decreased from SV 2010 to SV 1010. The process of selective production of DMA, using zeolite catalysts is described in detail in "Catalysts & Catalysis" (in Japanese), Vol. 29, No. 4, page 322.

As the methods for improving the DMA selectivity by using modified zeolite catalysts in the production of methylamines, the following have been known. Japanese Laid-Open Patent Publication No. 254256/1986 describes a method using a zeolite catalyst which is obtained by treating chabazite, erionite, zeolite, rho or zeolite ZK-5 with a compound comprising at least one element selected from silicon, aluminum, phosphorus and boron, thereby modifying the zeolite by depositing thereon these elements. Further, with respect to mordenite, the following methods have been known: Japanese Laid-Open Patent Publication No. 227841/1984 describes a method using a catalyst which is prepared by treating mordenite with water vapor; Japanese Laid-Open Patent Publication No. 179640/1994 describes a method using a catalyst which is prepared by silylating mordenite in the liquid phase; and Japanese Laid-Open Patent Publication No. 262540/1991 describes a catalyst which is prepared by treating mordenite with SiCl4 in the gaseous phase.

As processes for producing DMA by the use of Na-mordenite, a process for producing DMA selectively from MMA by using mordenite whose Na content has been adjusted is described in Japanese Laid-Open Patent Publication No. 46846/1981; and a process for selectively producing DMA by using mordenite whose Na content has been adjusted is described in Japanese Laid-Open Patent Publication No. 210050/1984.

Further, as a process for producing DMA, using high-silica mordenite, a process using Mg-containing high-silica mordenite is described in Japanese Laid-Open Patent Publication No. 9510/1994.

Thus, a variety of zeolite catalysts have been proposed as the catalysts for use in the production of methylamines. However, there is a demand for further improving the zeolite catalysts or for developing zeolite catalysts with which DMA can be produced at higher selectivity while the formation of TMA is being suppressed.

An object of the present invention is to provide a novel modified zeolite catalyst for use in the reaction between methanol or a methylamine mixture and ammonia to produce dimethylamine, which zeolite catalyst can eliminate the shortcoming of the conventional zeolite catalysts in that the DMA selectivity is drastically lowered when the conversion of methanol exceeds 95% and which can give higher DMA selectivity and lower TMA selectivity as well as higher methanol-consuming reaction activity.

DISCLOSURE OF THE INVENTION

We have made earnest studies in order to attain the above object, and, as a result, found that when a modified zeolite obtained by treating a zeolite with a chelating agent is employed as a catalyst in the production of dimethylamine, using methanol or a methylamine mixture and ammonia, extremely high DMA selectivity and low TMA selectivity can be obtained as well as high methanol-consuming reaction activity as shown in the examples, which will be given later. The present invention has been accomplished on the basis of this finding.

Thus, the present invention relates to a process for producing dimethylamine by the reaction of methanol with ammonia, of methanol and a methylamine mixture with ammonia, or of a methylamine mixture with ammonia in the gaseous phase in the presence of a catalyst, characterized in that a modified zeolite prepared by treating a zeolite with a solution containing a chelating agent is used as the catalyst.

BEST MODE FOR CARRYING OUT THE INVENTION

<Modified Zeolite>

The important point is that the modified zeolite catalyst for use in the process of the present invention is one treated with a chelating agent.

<Zeolite>

As the zeolite for use in the present invention, those zeolites which show shape selectivity in the reaction between ammonia and methanol to form methylamines, for instance, mordenite, chabazite, clinoptilolite, levynite, zeolite rho, zeolite A, FU-1, erionite, ZSM-5, ZSM-11, ZSM-21, and montmorillonite are preferred. Mordenite and chabazite are particularly preferred. Of these, proton-form mordenite or mordenite whose sodium content is in the range of 0.01 to 2.0 g for 100 g of the mordenite is preferred. More preferable mordenite is one in which the Si/Al atomic ratio has been adjusted to the range of 5.5 to 9.

<Chelating Agent>

In general, a chelating agent is defined as a compound having a multidentate ligand, capable of forming a chelate compound by being bound to a metallic ion, so that it is required to contain an acidic group (carboxyl group, sulfonyl group, phosphoryl group, hydroxyl group, etc.) having salt-forming capability, or an atomic group (amines, carbonyl group, etc.) having coordinating capability.

In the present invention, those chelating agents which can form water-soluble chelate compounds are preferred. Of these, preferable ones are those which have carboxyl group as the acidic group having salt-forming capability, and, in particular, those which have nitrogen atom as the atomic group having coordinating capability.

Polycarboxylic acids form one group in such chelating agents, and oxalic acid is a typical example thereof.

Nitrogen-containing carboxylic acids come under another group, and specific examples thereof include aminocarboxylic and pyridinecarboxylic acids.

The structure of an aminocarboxylic acid is such that nitrogen of ammonia or an amine is combined with at least one lower fatty mono- or polycarboxylic acid at the position other than the carboxyl group(s) therein. In the present invention, preferable aminocarboxylic acids are those which have a plurality of carboxyl groups, preferably 2 to 5 carboxyl groups, and a plurality of amino nitrogen atoms, preferably 2 or 3 amino nitrogen atoms.

Pyridinecarboxylic acids come under another group in the nitrogen-containing carboxylic acids. "Pyridine" herein includes not only pyridine itself, that is, non-substituted one, but also pyridines having a lower-alkyl substituent, that is, picoline, lutidine and collidine. "Pyridinecarboxylic acids" herein include not only those which have one carboxyl group but also those which have two or more carboxyl groups.

It is unclear whether or not the "chelating agents" used for modifying zeolites in the present invention can impart improved DMA-forming ability to the zeolites due to the chelating ability thereof. What is important is that those compounds which meet the above-described definition of chelating agent can impart improved DMA selectivity to zeolites.

As mentioned above, it is preferable to use an aminopolycarboxylic or pyridinecarboxylic acid as the chelating agent for use in the treatment of a zeolite. In particular, an aminopolycarboxylic acid having 2 to 6 carboxyl groups in one molecule thereof, or a pyridinedicarboxylic acid is preferably used. Further, particularly favorable results can be obtained by the use of an aminopolycarboxylic acid having 2 to 6 carboxyl groups in one molecule thereof and a maximum dissociation constant (pKn for the total number of carboxyl groups) of 9 to 12. The use of an aminopolycarboxylic acid having 3 to 6 carboxyl groups in one molecule thereof and a pKn of 9.5 to 12 is more preferred. Specific examples of such aminopolycarboxylic and pyridinedicarboxylic acids include those compounds which are shown in the Tables 1 and 2 given below. It is a matter of course that the aminopolycarboxylic and pyridinedicarboxylic acids used in the present invention also include the salts thereof because these salts are dissociated in working solutions into acidic anions.

TABLE 1

| Chelating Agent | Symbol | n* | pKn |
|---|---|---|---|
| Iminodiacetic acid | IDA | 2 | 9.12 |
| N-Methyliminodiacetic acid | MIDA | 2 | 9.65 |

TABLE 1-continued

| Chelating Agent | Symbol | n* | pKn |
|---|---|---|---|
| N-Hydroxyiminodiacetic acid | HIDA | 2 | 8.73 |
| Iminodipropionic acid | IDPA | 2 | 10.31 |
| Nitrilotriacetic acid | NTA | 3 | 9.73 |
| Beta-alaninediacetic acid | ALDA | 3 | 9.35 |
| Phosphonoethyliminodiacetic acid | EPDA | 4 | 10.46 |
| Carboxymethyliminodipropionic acid | CMIPA | 3 | 9.37 |
| Mercaptoethyliminodiacetic acid | MEIDA | 3 | 10.79 |
| Nitrilotripropionic acid | NTP | 3 | 9.30 |
| Aminoethyliminodiacetic acid | AEIDA | 2 | 11.05 |
| Iminodisuccinic acid | IDSN | 4 | 10.12 |
| Aspartic monoacetic acid | ASMA | 3 | 9.65 |
| Aspartic diacetic acid | ASDA | 4 | 9.18 |
| Ethylenediaminediacetic acid | EDDA | 2 | 9.57 |
| Ethylenediaminetetraacetic acid | EDTA | 4 | 10.23 |
| Ethylenediaminedipropionic acid | EDDP | 2 | 9.58 |
| Propanediaminetetraacetic acid | PDTA | 4 | 10.27 |
| 2-Hydroxy-1,3-propanediaminetetraacetic acid | HPDTA | 4 | 9.70 |
| Ethyletherdiaminetetraacetic acid | ETDTA | 4 | 9.47 |
| Ethylenediaminediacetic dipropionic acid | EDPA | 4 | 9.83 |
| Glycoletherdiaminetetraacetic acid | GEDTA | 4 | 9.46 |
| Ethylenediaminetetrapropionic acid | EDTP | 4 | 9.60 |
| Hydroxyethylethylenediaminetriacetic acid | HEDTA | 3 | 10.01 |
| 1,2-Propanediaminetetraacetic acid | MEDTA | 4 | 10.84 |

*n: Number of acid groups

TABLE 2

| Chelating Agent | Symbol | n* | pKn |
|---|---|---|---|
| Ethylenediaminedisuccinic acid | EDDS | 4 | 10.40 |
| Propanediaminedisuccinic acid | PDDS | 4 | 10.53 |
| 1,2-Cyclohexanediaminetetraacetic acid | 1,2-CDTA | 4 | 11.70 |
| 1,3-Cyclohexanediaminetetraacetic acid | 1,3-CDTA | 4 | 10.91 |
| 1,4-Cyclohexanediaminetetraacetic acid | 1,4-CDTA | 4 | 10.86 |
| Diethylenetriaminepentaacetic acid | DTPA | 5 | 10.58 |
| Bis(ethyl iminodiacetate)methylamine | MDTTA | 4 | 10.89 |
| Triethylenetetraminehexaacetic acid | TTHA | 6 | 10.33 |
| 2,6-Pyridinedicarboxylic acid | 2,6-PDCA | 2 | — |
| 2,4-Pyridinedicarboxylic acid | 2,4-PDCA | 2 | — |
| 2,3-Pyridinedicarboxylic acid | 2,3-PDCA | 2 | — |

*n: Number of acid groups

<Treatment for Modification>

The treatment of a zeolite is typically carried out by the use of a solution of a chelating agent. It is preferable to use water as the solvent. In general, the pH of a solution of a chelating agent in water is adjusted to approximately 3 to 7, and a zeolite is dipped in the solution, or a mixture of a zeolite and the solution is stirred. Alternatively, the chelating agent solution is allowed to flow through a zeolite. The amount of the chelating agent used is, in general, from 0.001 to 20 mol for 100 g of the zeolite; the concentration of the chelating agent is from 0.01 to 20 mol/liter; the treatment temperature is from room temperature to 100° C.; and the treatment time is from 1 to 500 hours.

Zeolites in any condition or shape can be treated with a chelating agent for the modification thereof as long as they are existing as zeolites.

As mentioned above, one of the typical methods of modification is that a zeolite whose sodium content has been adjusted to a predetermined level upon necessity is shaped into granules, pellets, or one suitable for a catalyst, and the resulting zeolite is brought into contact with a solution of a chelating agent (specifically, by means of impregnation, spraying, or flow contact).

One of the other methods is such that a zeolite which has not yet reached the final shape suitable for a catalyst is treated with a chelating agent for modification. Specifically, this method can be effected, for example, in such a manner that after zeolite powder whose sodium content has upon necessity been adjusted to a predetermined level is impregnated or sprayed or brought into flow contact with a solution of a chelating agent, it is shaped into granules, pellets or one suitable for a catalyst; or a manner in that during the step of adjusting the sodium content of zeolite powder, the zeolite is treated with a chelating agent, and the resultant is then subjected to granulation or pelleting. Of these, a preferable method of modification is the former one, that is, the method in which a zeolite in such a shape that it can be actually used as it is as a catalyst is impregnated or brought into flow contact or sprayed with a solution of a chelating agent, and the resultant is subjected to drying.

Modified zeolites obtained by treating zeolites with a chelating agent such as an aminopolycarboxylic or pyridinecarboxylic acid can give much higher DMA selectivity as compared with those obtained by treating zeolites with a chelating agent other than the above, for example, a polycarboxylic acid such as oxalic acid. In particular, modified mordenite obtained by treating mordenite with an aminopolycarboxylic acid having 2 to 6 carboxyl groups in one molecule thereof and a maximum dissociation constant (pKn for the number of carboxyl groups) of 9 to 12 can give much higher DMA selectivity.

Further, particularly excellent effects can be obtained when mordenite whose Si/Al atomic ratio is in the range of 5.5 to 9.0 is subjected to the treatment using a chelating agent. The reaction for producing dimethylamine according to the present invention is carried out at a temperature of 230° to 350° C., preferably 250° to 330° C. It is preferable to carry out the reaction under the following conditions; the pressure is from normal pressure to 50 $Kg/cm^2G$, preferably from 5 to 30 $Kg/cm^2G$; the N/C ratio (the ratio of the number of nitrogen atoms to that of carbon atoms in the reaction system) is from 1 to 2.5; the space velocity is from 600 to 2,000/hr; and the conversion of methanol is from 80 to 98%.

EXAMPLES

The present invention will now be explained more specifically with reference to the following Examples and Comparative Examples. However, the present invention is not limited by the following examples in any way.

EXPERIMENTAL METHOD OF REACTION

A catalyst was placed in a 1/2B stainless steel reaction tube having a length of 800 mm. A 1:1 (weight basis) mixture of ammonia and methanol was introduced into the reaction tube at the rate of 1.0 g/min, and the reaction between the two compounds was carried out at a temperature of 320° C. under a pressure of 18 $Kg/cm^2G$.

EXAMPLES 1 to 13

Na-form mordenite powder was placed in a 3-N ammonium nitrate solution whose amount was 20 times the amount of the mordenite, and the mixture was boiled under reflux for 6 hours. The mordenite was separated from the mixture by filtration. A 3-N ammonium nitrate solution was added again to the mordenite, and the mixture was boiled under reflux for 6 hours. This was repeated 4 times in total. The mordenite separated by filtration was washed with water, dried at 130° C. for 6 hours, and calcined at 450° C. for 3 hours, thereby obtaining H-form mordenite. 100 g of this H-form mordenite was placed in 1 liter of a 1-N sodium nitrate solution, and the mixture was boiled under reflux at 40° C. for 20 hours, whereby mordenite containing 0.4% of sodium was prepared. This mordenite was molded into cylindrical pellets having a diameter of 3 mm. Successively, 100 g of the pelleted mordenite was dipped at 80° C. for 8 hours in a solution which had been prepared by adding 0.269 mol of one of various chelating agents shown in Table 3 in 500 g of water, and dissolving the chelating agent in the water by adjusting the pH of the solution to 4 to 5 by using sodium hydroxide. The mordenite was separated by filtration, washed with water, dried at 120° C. for 4 hours, and then calcined at 500° C. for 4 hours.

Ammonia and methanol were reacted with each other to produce dimethylamine by the use of the above-obtained mordenite catalyst. As a result, a methylamine mixture having the composition shown in Tables 3 and 4 was obtained.

TABLE 3

| Example | Chelating Agent | Space Velocity (1/hr) | Conversion of Methanol (%) | Each Methylamine (%) Contained in Methylamines formed | |
|---|---|---|---|---|---|
| | | | | DMA | TMA |
| 1 | EDTA | 3220 | 88.9 | 56.3 | 4.8 |
| | | 1570 | 98.0 | 57.3 | 8.0 |
| 2 | NTA | 3230 | 87.8 | 55.5 | 4.5 |
| | | 1550 | 97.5 | 58.1 | 7.0 |
| 3 | PDTA | 3160 | 87.9 | 55.7 | 4.2 |
| | | 1530 | 97.5 | 58.0 | 7.0 |
| 4 | EDDS | 3270 | 87.2 | 55.5 | 3.7 |
| | | 1630 | 97.4 | 58.9 | 4.5 |
| 5 | EDDA | 3240 | 86.1 | 55.1 | 4.1 |
| | | 1600 | 96.9 | 58.3 | 6.3 |
| 6 | HPDTA | 3180 | 88.4 | 56.0 | 4.7 |
| | | 1580 | 97.7 | 57.7 | 7.4 |
| 7 | HEDTA | 3160 | 88.9 | 56.0 | 4.8 |
| | | 1640 | 97.7 | 57.8 | 7.4 |

TABLE 4

| Example | Chelating Agent | Space Velocity (1/hr) | Conversion of Methanol (%) | Each Methylamine (%) Contained in Methylamines formed | |
|---|---|---|---|---|---|
| | | | | DMA | TMA |
| 8 | 1,2-DTA | 3270 | 89.8 | 56.3 | 5.0 |
| | | 1650 | 97.9 | 57.6 | 7.9 |
| 9 | TTHA | 3210 | 89.0 | 56.0 | 4.4 |
| | | 1630 | 97.6 | 58.5 | 6.9 |
| 10 | DTPA | 3210 | 87.8 | 56.2 | 4.5 |
| | | 1600 | 97.6 | 57.7 | 7.9 |
| 11 | GEDTA | 3150 | 87.6 | 55.3 | 7.7 |
| | | 1600 | 97.6 | 56.7 | 9.1 |
| 12 | 2,6-PDCA | 3220 | 89.0 | 55.9 | 4.3 |
| | | 1580 | 96.9 | 58.7 | 6.4 |
| 13 | HIDA | 3250 | 89.5 | 54.5 | 9.3 |
| | | 1610 | 97.8 | 50.3 | 14.5 |

EXAMPLE 14

Chabazite powder containing approximately 20% of erionite was placed in a sodium nitrate solution whose amount was 20 times the amount of the chabazite powder, and the mixture was boiled under reflux for 4 hours. The chabazite was separated by filtration, washed with water, dried at 130° C. for 6 hours, and then calcined at 450° C. for 3 hours. The resulting chabazite was molded into cylindrical pellets having a diameter of 3 mm. Successively, the pelleted chabazite was treated with a chelating agent in the same manner as in Example 1. It is noted that EDTA was used as the chelating agent.

Ammonia and methanol were reacted with each other to produce dimethylamine by the use of the above-obtained chabazite catalyst. As a result, a methylamine mixture having the composition shown in Table 5 was obtained.

TABLE 5

| Space Velocity | Conversion of Methanol | Each Methylamine (%) Contained in Methylamines formed | | |
|---|---|---|---|---|
| (1/hr) | (%) | MMA | DMA | TMA |
| 1200 | 94.5 | 35.8 | 50.4 | 13.8 |

COMPARATIVE EXAMPLE 1

Mordenite containing 0.4% of sodium was prepared in the same manner as in Example 1, and molded into cylindrical pellets having a diameter of 3 mm to give a catalyst. It is noted that the treatment using a chelating agent was not carried out.

Ammonia and methanol were reacted with each other to produce dimethylamine by the use of the above-obtained mordenite catalyst. As a result, a methylamine mixture having the composition shown in Table 6 was obtained.

TABLE 6

| Space Velocity | Conversion of Methanol | Each Methylamine (%) Contained in Methylamines formed | | |
|---|---|---|---|---|
| (1/hr) | (%) | MMA | DMA | TMA |
| 1400 | 96.8 | 30.7 | 34.1 | 35.2 |

COMPARATIVE EXAMPLE 2

Chabazite was prepared in the same manner as in Example 14, and molded into cylindrical pellets having a diameter of 3 mm to obtain a catalyst. It is noted that the treatment using a chelating agent was not carried out.

Ammonia and methanol were reacted with each other to produce dimethylamine by the use of the above-obtained chabazite catalyst. As a result, a methylamine mixture having the composition shown in Table 7 was obtained.

TABLE 7

| Space Velocity | Conversion of Methanol | Each Methylamine (%) Contained in Methylamines formed | | |
|---|---|---|---|---|
| (1/hr) | (%) | MMA | DMA | TMA |
| 1200 | 95.7 | 32.3 | 30.4 | 37.3 |

EXAMPLE 15

Mordenite containing 0.4% of sodium was prepared in the same manner as in Example 1, and molded into cylindrical pellets having a diameter of 3 mm. Successively, 100 g of this mordenite was dipped in 600 ml of a 2 mol/liter solution of oxalic acid serving as a chelating agent, at 70° C. for 1 hour. The mordenite was separated by filtration, washed with water, dried at 130° C. for 4 hours, and then calcined at 500° C. for 3 hours.

Ammonia and methanol were reacted to produce dimethylamine by the use of the above-obtained mordenite catalyst. As a result, a re having the composition shown in Table 8 was obtained.

TABLE 8

| Space Velocity | Conversion of Methanol | Each Methylamine (%) Contained in Methylamines formed | | |
|---|---|---|---|---|
| (1/hr) | (%) | MMA | DMA | TMA |
| 1600 | 98.1 | 31.0 | 43.3 | 25.7 |

INDUSTRIAL APPLICABILITY

The modified zeolite catalysts prepared by the treatment using a chelating agent according to the present invention have, as catalysts for use in the production of methylamines, the effects of improving the DMA selectivity and suppressing the TMA selectivity while maintaining the methanol-consuming reaction activity high. Therefore, when dimethylamine is produced by the reaction between methanol and/or a methylamine mixture and ammonia, the modified zeolite catalysts of the invention can give high dimethylamine selectivity unlike the conventional zeolite catalysts even when the conversion of methanol is as high as 98%, and can have a greatly improved duration of life.

We claim:

1. In a process for producing dimethylamine by the reaction of methanol with ammonia, of methanol and a methylamine mixture with ammonia, or of a methylamine mixture with ammonia in the gaseous phase in the presence of a catalyst, the improvement which comprises the use as the catalyst of a modified zeolite prepared by treating a zeolite with a solution containing a chelating agent, wherein the chelating agent is an aminopolycarboxylic acid or salt thereof.

2. The process for producing dimethylamine according to claim 1, wherein the chelating agent is a pyridinecarboxylic acid.

3. The process for producing dimethylamine according to claim 1, wherein the chelating agent is an aminopolycarboxylic acid having 2 to 6 carboxyl groups or a pyridinedicarboxylic acid.

4. The process for producing dimethylamine according to claim 1, wherein the chelating agent is an aminopolycarboxylic acid having 2 to 6 carboxyl groups and a maximum dissociation constant (pKn for the total number of carboxyl groups) of 9 to 12.

5. The process for producing dimethylamine according to claim 1, wherein the zeolite is mordenite or chabazite.

6. The process for producing dimethylamine according to claim 5, wherein the zeolite is mordenite whose sodium content is 2.0.g or less per 100 g of the mordenite.

7. The process for producing dimethylamine according to claim 5, wherein the zeolite is mordenite whose Si/Al atomic ratio is in the range of 5.5 to 9.

8. The process for producing dimethylamine according to claim 1, wherein the gas phase reaction is carried out at a temperature of from 200° to 350° C., a pressure of from 5 to 50 atmospheres, an N/C ratio of from 1 to 2.5, and a conversion of methanol of from 80 to 98%.

9. The process for producing dimethylamine according to claim 5, wherein the zeolite is a mordenite whose sodium content is 0.01 to 2.0 g per 100 g of the mordenite.

* * * * *